(12) United States Patent
Chmielewski et al.

(10) Patent No.: US 11,045,108 B2
(45) Date of Patent: Jun. 29, 2021

(54) MAGNETIC RESONANCE IMAGING RECEIVE COIL ASSEMBLY

(71) Applicant: ViewRay Technologies, Inc., Oakwood Village, OH (US)

(72) Inventors: Thomas Chmielewski, Aurora, OH (US); James F. Dempsey, Atherton, CA (US)

(73) Assignee: VIEWRAY TECHNOLOGIES, INC., Oakwood Village, OH (US)

( * ) Notice: Subject to any disclaimer, the term of this patent is extended or adjusted under 35 U.S.C. 154(b) by 1373 days.

(21) Appl. No.: 14/555,205

(22) Filed: Nov. 26, 2014

(65) Prior Publication Data

US 2016/0146911 A1    May 26, 2016

(51) Int. Cl.
*A61B 5/055* (2006.01)
*A61N 5/10* (2006.01)
*G01R 33/34* (2006.01)
*G01R 33/48* (2006.01)
*G01R 33/3415* (2006.01)

(52) U.S. Cl.
CPC ............ *A61B 5/055* (2013.01); *A61N 5/1049* (2013.01); *G01R 33/34007* (2013.01); *G01R 33/3415* (2013.01); *G01R 33/4808* (2013.01); *A61N 2005/1055* (2013.01)

(58) Field of Classification Search
CPC .................. A61B 5/055; A61N 5/1049; A61N 2005/1055; G01R 33/34007; G01R 33/3415; G01R 33/4808
See application file for complete search history.

(56) References Cited

U.S. PATENT DOCUMENTS

| | | | | |
|---|---|---|---|---|
| 6,060,882 A | * | 5/2000 | Doty | G01R 33/34046 324/318 |
| 6,366,798 B2 | * | 4/2002 | Green | A61N 5/1042 378/65 |
| 6,930,480 B1 | * | 8/2005 | Fujita | G01R 33/34046 324/309 |
| 2008/0129296 A1 | * | 6/2008 | Fischer | G01R 33/34084 324/318 |
| 2009/0021256 A1 | * | 1/2009 | Soutome | G01R 33/34007 324/318 |
| 2011/0012593 A1 | * | 1/2011 | Shvartsman | G01R 33/3806 324/307 |

(Continued)

*Primary Examiner* — Bo Joseph Peng
(74) *Attorney, Agent, or Firm* — Pillsbury Winthrop Shaw Pittman LLP (57) ABSTRACT

A radiofrequency receive coil assembly can include a first conductive loop and a second conductive loop electrically connected at a node. The first and second conductive loops can extend into a treatment beam region of the radio frequency receive coil assembly through which one or more beams of ionizing radiation pass. The first conductive loop and the second conductive loop can overlap each other to provide electromagnetic isolation and/or can use a common conductor combined with a shared capacitor to provide electromagnetic isolation, with the shared capacitor or other electrical components, as well as any conductive loop overlaps, being positioned outside of the treatment beam region. These features can, among other possible advantages, minimize and homogenize attenuation of the beams of ionizing radiation by the radiofrequency receive coil assembly.

18 Claims, 8 Drawing Sheets

(56) References Cited

U.S. PATENT DOCUMENTS

2011/0215807 A1\* 9/2011 Misic .................. G01R 33/341
324/322
2013/0027040 A1\* 1/2013 Alagappan ....... G01R 33/34007
324/322

\* cited by examiner

MAGNETIC RESONANCE IMAGING RECEIVE COIL ASSEMBLY

TECHNICAL FIELD

The subject matter described herein relates generally to electromagnetic pick-up coils, such as for example magnetic resonance imaging (MRI) receive coils.

BACKGROUND

A receive coil (which is also sometimes referred to as a receiver coil or a radiofrequency coil) converts electromagnetic radiation to an electrical current. By measuring the electrical current in a distribution of coils, the distribution of electromagnetic radiation from a source may be determined.

Generally, in an MRI system, a substantially uniform main magnetic field, $B_0$, is created to cover the entire region of an area or volume to imaged. For example, a subject may be positioned within an MRI scanner which forms the strong magnetic field. In most medical applications, protons (hydrogen atoms) in tissues containing water molecules are used to create a signal that is processed to form the image. The static magnetic field tends to align the proton spins (e.g. their magnetic dipoles) in the direction of the field where they precess around the field's axis. Energy from an oscillating magnetic field is temporarily applied to the patient at an appropriate resonant frequency to excite the protons, thereby causing a flip of their spin states. The excited hydrogen atoms emit a radio frequency signal, which is measured by a receive coil. The contrast between different tissues is determined by the rate at which excited atoms return to the equilibrium state.

SUMMARY

In one aspect, a radiofrequency receive coil assembly for use in an MRI system can have a first conductive loop and a second conducting loop, extending into a treatment beam region, and electrically connected to each other at a node. The first conductive loop and the second conductive loop are made of a conductive material and lie in approximately the same plane and are of approximately equal thickness normal to that plane. Also, the first conductive loop and the second conductive loop do not overlap each other in the treatment beam region. The treatment beam passes through only a single layer of the conductive material.

In an interrelated aspect, a magnetic resonance imaging-radiotherapy system includes a magnetic resonance imaging system having a radiofrequency receive coil assembly, as described above.

In further interrelated aspect, a method for delivering radiotherapy treatment to a target region while imaging the target region includes directing one or more beams of ionizing radiation at the target region disposed within an MRI device. The beams of ionizing radiation that pass through a treatment beam region undergo uniform attenuation by the radiofrequency receive coil assembly. The radiofrequency receive coil assembly detects an MRI signal from the target region.

In some variations one or more of the following features can optionally be included in any feasible combination.

The radiofrequency receive coil can include an insulating region within the treatment beam region, where the radiofrequency receive coil has a layer that causes the attenuation of beams of ionizing radiation passing through the insulating region to be approximately equal to the attenuation of beams of ionizing radiation passing through the conductive material of the radiofrequency receive coil.

A common conductor and a shared capacitor can be included, to provide electrical isolation, between the first conducting loop and the second conducting loop. The capacitor, vias, or other electrical components can be located outside the treatment beam region.

There can also be a substrate that supports the first conducting loop, the second conducting loop, and the insulating region. The substrate and/or the insulating layer can be constructed of polyimide. The first conducting loop and/or second conducting loop can be constructed from copper, silver, and/or aluminum. Also, a third conducting loop can be located on the opposite side of the substrate from the first conducting loop and the second conducting loop.

The first conducting loop and the second conducting loop can be separated by a linear distance sufficient to cause the mutual inductance between the first conducting loop to fall below 5%, or below 1%.

The magnetic resonance imaging-radiotherapy system can have a split magnetic resonance imaging system. The split magnetic resonance imaging system can have first and second magnet housing separated by a gap region, a gantry disposed in the gap region, at least one radiotherapy head disposed on and moveable with the gantry, and a patient couch configured to support a subject within the first and second magnet housings. Also, the split magnetic resonance imaging system can have the radiofrequency receive coil assembly.

The beams of ionizing radiation can be generated by a radioisotope source and/or a linear accelerator.

The second conducting loop can be electrically connected to the first conducting loop at a node. Also, the first conducting loop and the second conducting loop can be approximately in a same plane, and both have at least approximately equal thickness normal to the same plane. They can also not overlap each other in the treatment beam region, such that the beams of ionizing radiation pass through only a single layer of the conductive material in traversing the beam region.

The beams can also be directed to, passed through, and detected from the treatment beam region by the magnetic resonance imaging-radiotherapy system.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Use of combined MRI-radiotherapy systems that are capable of imaging a treatment area or volume of a subject concurrently with the delivery of ionizing radiation to the treatment area or volume is increasing. Currently available MRI receive coils may not be optimal for use with such systems. For example, receive coils can include overlaps, vias, or the like between adjacent coil segments. The presence of these features within a radiation beam of a radiotherapy system can be undesirable because of detuning of the coil element that can occur over time (e.g. as a result of capacitive components of the coil being exposed to radiation) and/or because of non-uniformities these features can cause in the radiation beam.

Implementations of the current subject matter can include approaches for decoupling components of a receive coil from one another while keeping the components out of the path of a radiation beam of a radiotherapy system. Receive coils consistent with the current subject matter can cause substantially less interference with a treatment beam passing through them compared to currently available approaches, for example by applying uniform attenuation to a treatment beam passing through them, thereby allowing the radiation reaching the patient to remain uniform. Receive coils consistent with the current subject matter can also include decoupling elements that allow for uniform attenuation without degrading the Q-factor or other performance factors of receive coils for the coil circuitry.

Figure 1:
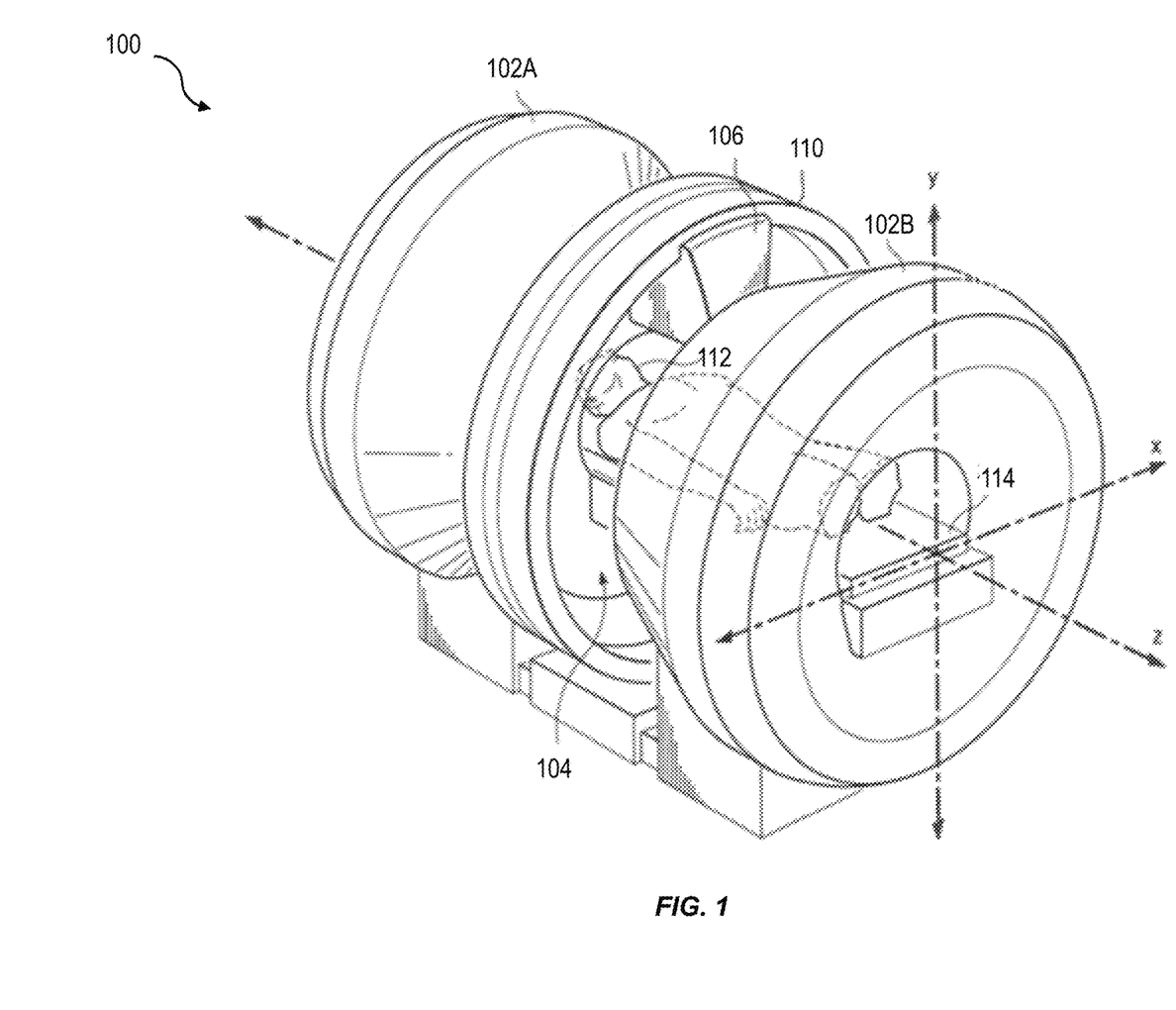
FIG. 1 shows a perspective view of a split MRI system.

FIG. 1 shows a perspective view of an example of a split or "open" MRI system 100. The split MRI system includes first and second magnet housings 102A and 102B, which are separated by a gap region 104. An instrument 106 is mounted in the gap region 104 on a gantry 110. The instrument can include one or more radiation sources for delivering radiation to a target region. A patient 112 is shown in FIG. 1 positioned on a patient couch 114 inside of the first and second magnet housings 102A, 102B and such that the gantry 110 can cause rotation of the instrument 106 to different positions relative to the patient 112 on the patient couch 114. For example, the gantry 110 can be used to reposition the instrument 106 about the patient 112 (i.e. at different angles of rotation about the Z-axis shown in FIG. 1).

While only a single assembly is shown as the instrument 106 in FIG. 1, implementations of the current subject matter can include multiple assemblies mounted on the gantry 110, such as for example, multiple radiation emitters and/or multi-leaf collimator devices. For example, some implementations can include three radiation head assemblies (not shown in FIG. 1) mounted in the gap 104, distributed about the Z-axis, and rotatable about the Z-axis on the gantry 110. A receive coil assembly as disclosed herein can be used in any type of MRI, with or without the use of an associated instrument 106. Furthermore, for systems utilizing an instrument 106, such instruments are not limited to one or more radiation therapy devices such as radiation sources or linear particle accelerators (LINACs), but can include any type of instrument used with an MRI.

Figure 2:
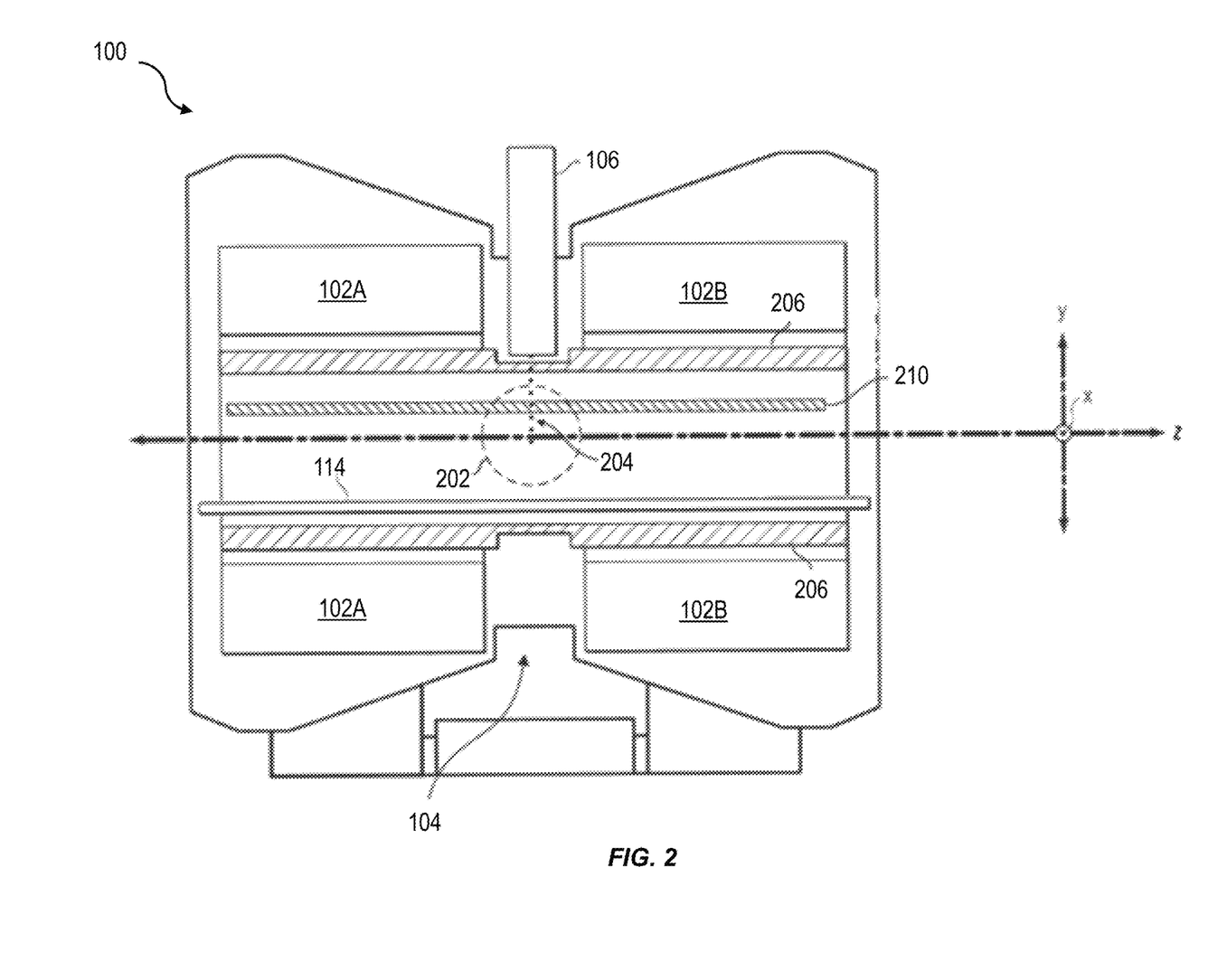
FIG. 2 shows a simplified cross-sectional view of the split MRI system shown in FIG. 1.

FIG. 2 shows a cross-sectional view of the system 100 shown in FIG. 1. The system 100 can be used to image a target region 202 (e.g. a volume or area within the patient (not shown in FIG. 2), which can be position above the patient couch 114, while the instrument 106 can be used to emit radiation 204 for simultaneously performing some form of treatment to the patient within a target region 202. The system 100 can also include a radiofrequency transmit coil assembly 206 for transmitting RF signals used for imaging. The system 100 can further include a RF receive coil assembly 210 that extends across the gap 104. Implementations of the RF receive coil assembly 210 are described in greater detail below.

The system 100 can further include additional components that are not shown in FIG. 1 or FIG. 2, such as for example gradient coils, one or more shim coils, and the like. The coordinate system used in the figures and throughout this disclosure refers to the longitudinal axis through the first and second magnet housings 102A and 102B. The X-axis extends perpendicular to the Z-axis and from side to side of the first and second magnet housings 102A and 102B, and the Y-axis extends perpendicular to the X-axis and the Z-axis and from the bottom to the top of the first and second magnet housings 102A and 102B.

As shown in FIG. 2, the RF receive coil assembly 210 extends between the instrument 106 and the target region 202. Accordingly, in implementations in which the instrument 106 includes a radiation emitting device such as those used with a radiotherapy system, a portion of the RF receive coil assembly 210 will be in the path of the radiation 204 that directed from the instrument 106 toward the target region 202. Use of existing RF coil assembly in such a position can be undesirable, both for MRI operation and for operation of the radiation therapy device as well as for other systems that could be implemented as the instrument 106. For example, some RF receive coils include structure that may interferes with a radiation therapy beam 204 passing through the RF receive coil from the instrument 106, potentially attenuating the beam to the point where the RF receive coil completely prevents treatment from being performed. Implementations of the current subject matter include configurations of a RF receive coil and methods for using such RF receive coils that can allow MRI imaging without interference to the operation of an instrument 106. For example, a RF receive coil consistent with the current subject matter can allow for MRI imaging without causing variations in attenuation to a treatment beam being emitted from instrument 106 through different portions of the RF receive coil 210.

Figure 3:
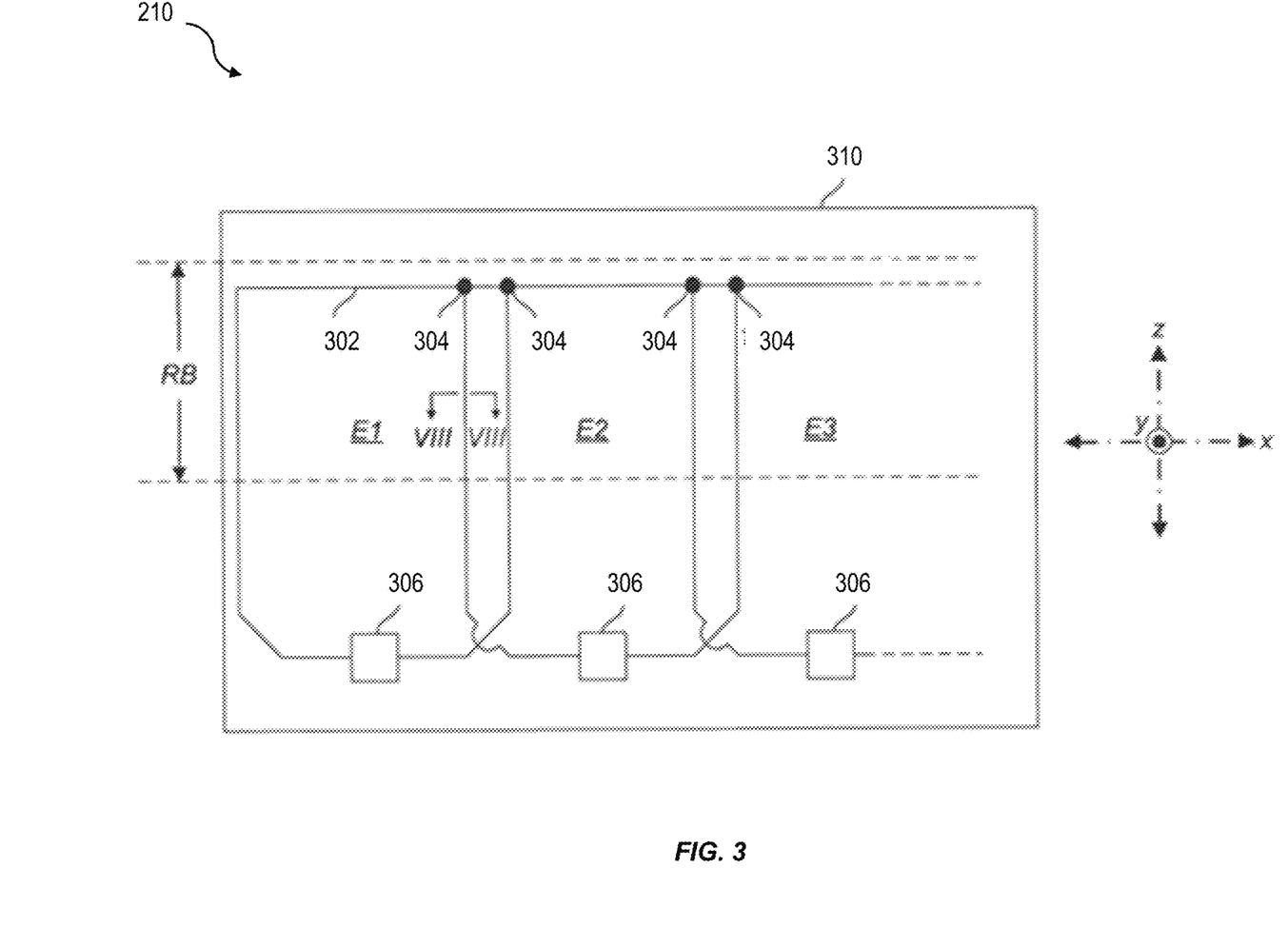
FIG. 3 shows a plan view of a circuit layout of an RF receive coil that includes 1×n array of MRI receive coil elements according to the present disclosure.

FIG. 3 shows a plan view of a circuit layout of a 1×n implementation of a RF receive coil 210 consistent with implementations of the current subject matter. The RF receive coil 210 includes a 1×n array of receive coil elements E1, E2, and E3. The RF receive coil 210 can include a series of conductive lines 302, which can be formed of an electrically-conductive material, including but not limited to copper, silver, aluminum, or any other conducting material. The conductive lines 302 can form loops, one for each of the receive coil elements E1-E3, which are electrically connected at a plurality of nodes 304. While three receive coil elements E1, E2, and E3 are shown, any number of receive coil elements can be included. The conductive lines 302 can also be connected to various RF receive coil components, shown generally as components block 306, and which can include one or more RF receive coil components. For example, the components block 306 can include interface electronics that provide one or more of tuning, matching, pre-amplification, transmit decoupling, and the like.

The conductive lines 302 can be formed on a substrate 310, one example of which is a printed circuit board (PCB). A PCB or other substrate 310 consistent with implementations of the current subject matter can be formed of insulating materials, such as, for example, polyimide film (e.g., KAPTON available from Dupont of Wilmington, Del.). In the illustrated implementation, the RF receive coil assembly 210 can be at least approximately planar in the region RB through which the treatment beam 204 passes and can have an at least approximately similar thickness in a direction normal to the plane in which they lie. The region RB of the RF receive coil 210 is free of components, vias, or overlapping conductors. In this manner, at any point in the region RB, the treatment beam 204 passes through only a single layer of the conducting material from which the conductive lines 302 are formed. Accordingly, the attenuation of the treatment beam 204 is uniform at all points in the region RB where the treatment beam encounters a conducting line 302. In the areas of the region RB where the treatment beam 204 does not encounter a conducting line 302, the attenuation can differ. However, consistent with implementations of the current subject matter, attenuation to the treatment beam 204 in the parts of the region RB where the treatment beam 204 does not encounter a conducting line 302, the attenuation can be made at least approximately uniform with the attenuation due to the conducting lines 302 by thickening a supporting substrate and or adding additional attenuating materials in areas of the region RB of the RF receive coil 210 that surround the conductive lines 302.

Figure 4:
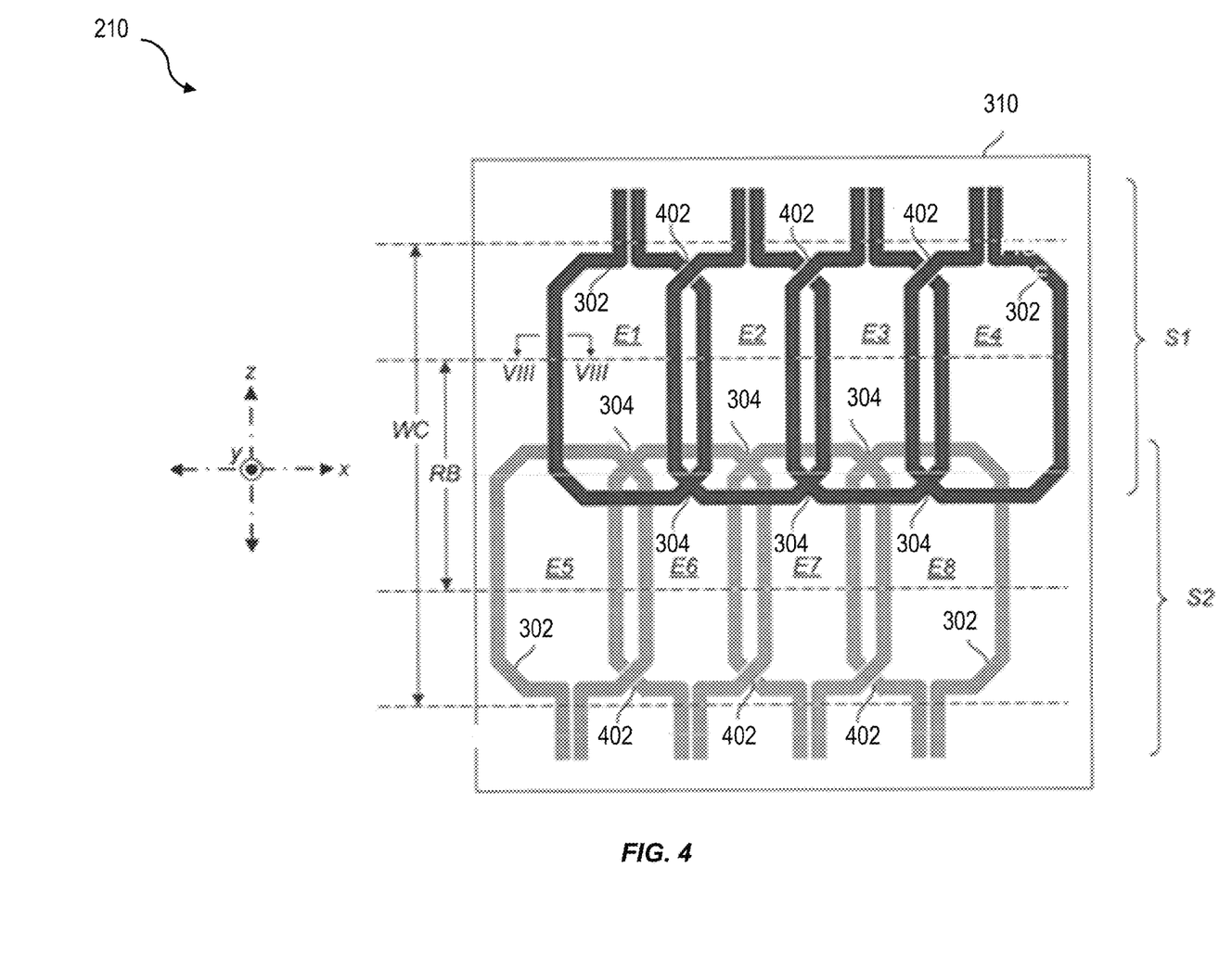
FIG. 4 shows a plan view of a circuit layout of an RF receive coil that includes two 1×n arrays of MRI receive coil elements according to the present disclosure.

FIG. 4 shows an implementation of a RF coil 210, which includes two of the 1×n arrays S1, S2 of the receive coil elements shown in FIG. 3. A first of the 1×n arrays S1, which includes the receive coil elements E1-E4, is formed on one side of the substrate 310, and a second of the 1×n arrays S2, which includes the receive coil elements E5-E8, is formed on an opposite side of the substrate 310. As with the implementation shown in FIG. 3, the implementation shown in FIG. 4 includes a treatment beam area RB where there are no components, vias, or overlapping conductors on either side of the substrate 310. Also, the region WC illustrates a worst-case region where radiation may stray beyond the expected treatment beam area RB without harming the coil 210 or being subjected to components that may cause non-uniformities in the treatment beam 204. Adding an appropriate thickness of the substrate 310 on each side of or to compensate for the conductive lines 302 can yield a uniform attenuation to the treatment beam 204 throughout the necessary volume.

While all of the circuit elements on each side of the substrate 310 are electrically connected together, they can be electromagnetically isolated by overlapping regions 402. For example, where the conducting lines 302 overlap at the overlapping regions 402, jumpers can be soldered into place to complete the loops while isolating from the adjacent loop. Each loop can be broken at the overlapping region 402, as shown in the gaps in the conducting lines 302. To complete the circuit over the loop gap, jumpers can electrically connect the gap in, for example loop E1, while being insulated from the adjacent loop, for example loop E2. The overlapping of the coils can be adjusted to reduce or minimize the mutual inductance of adjacent loops. This can be done for loop sets that are co-planar, as well as coil sets that are on opposite sides of the substrate 310. In one implementation, the linear distance from adjacent loop centers (e.g. the geometric center of the rectangular loop) can be varied to have nearest neighbor mutual inductance below 5% of the inductance of each individual loop. In another implementation, the linear distance from adjacent loop centers can be varied to have nearest neighbor mutual inductance below 1% of the inductance of each individual loop.

Figure 5:
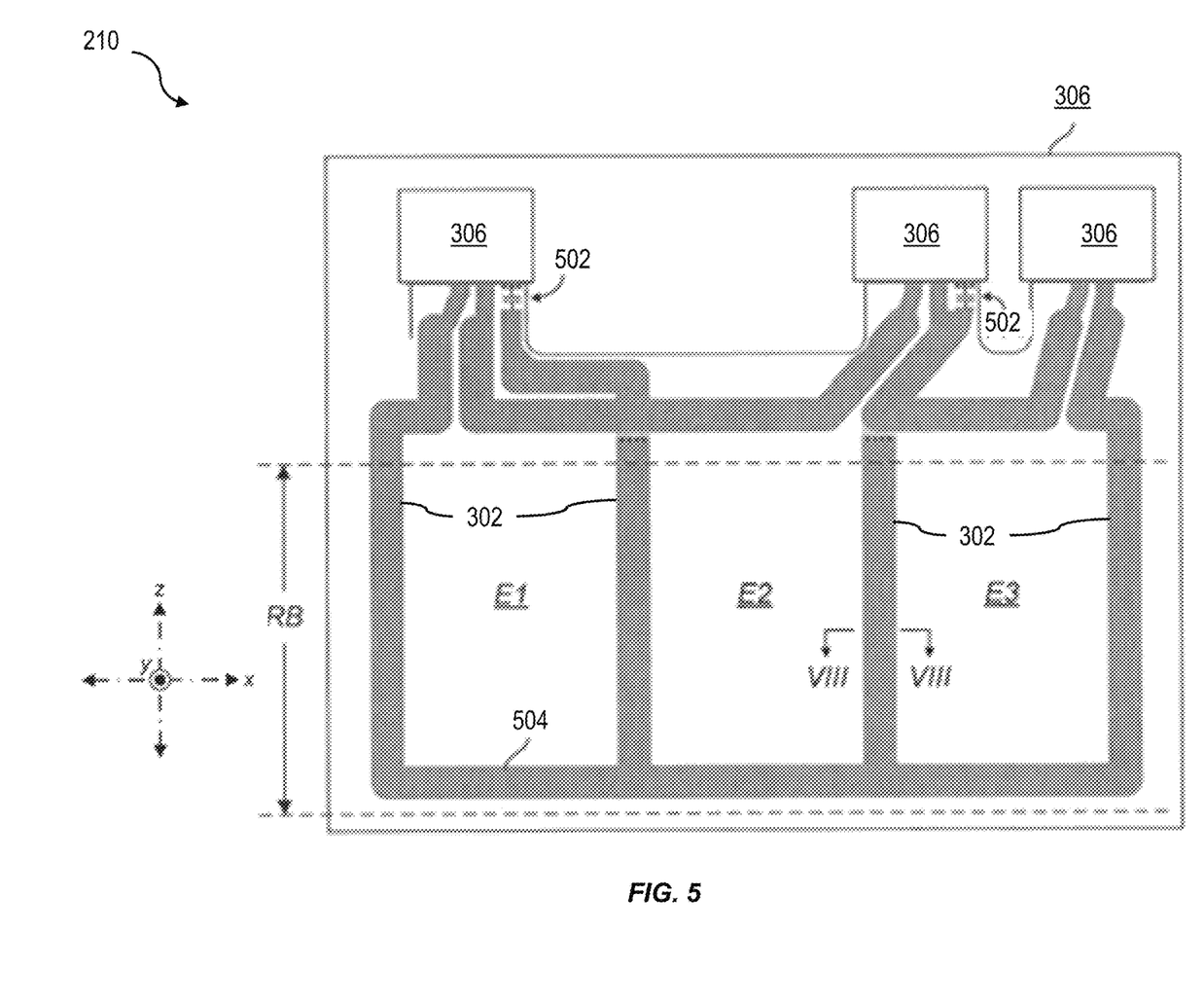
FIG. 5 shows a plan view of a circuit layout of an RF receive coil that includes 1×n array of MRI receive coil elements having shared capacitors according to the present disclosure.
Figure 6:
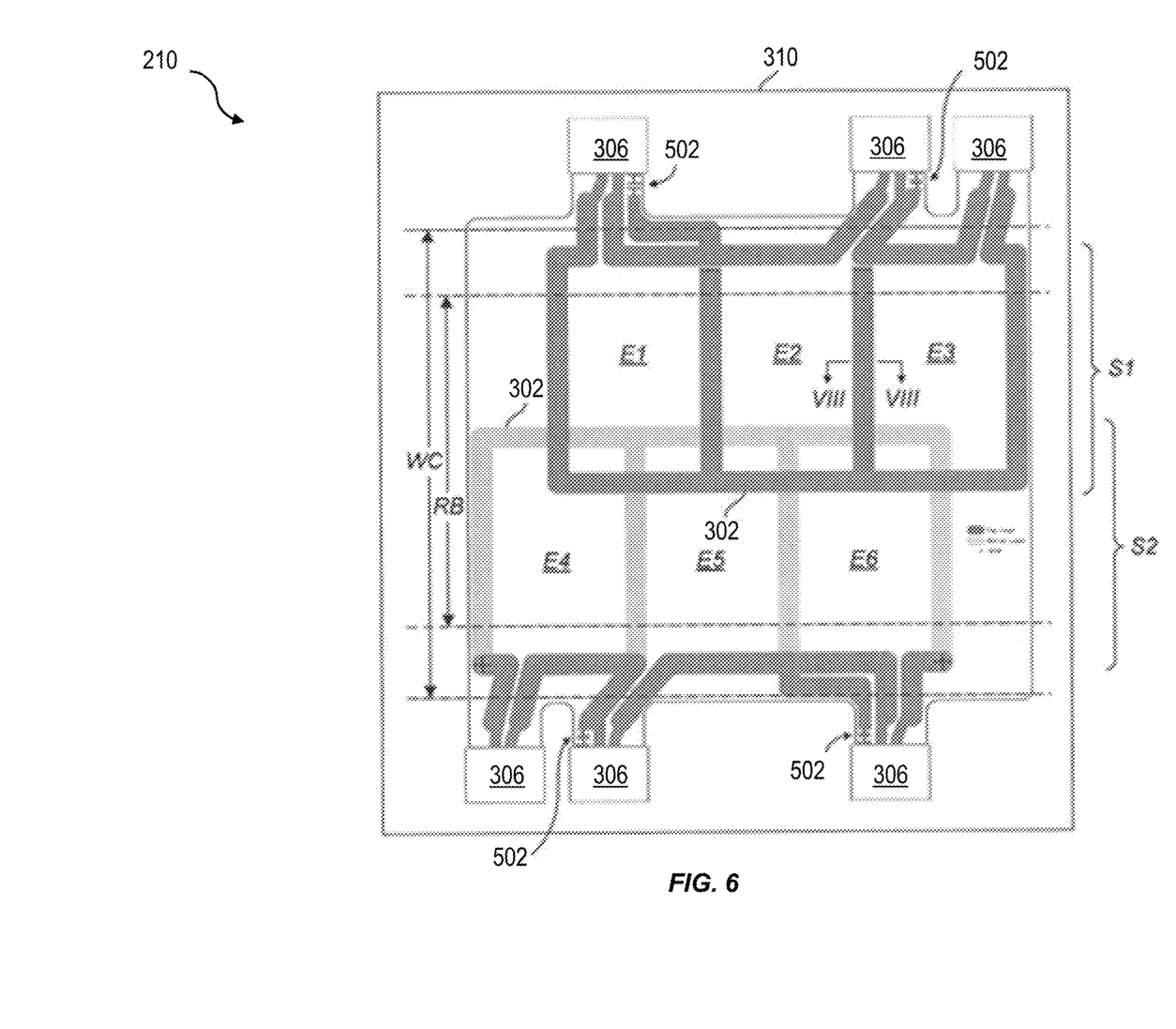
FIG. 6 shows a plan view of a circuit layout of an RF receive coil that includes two 1×n arrays of MRI receive coil elements having shared capacitors according to the present disclosure.
Figure 7:
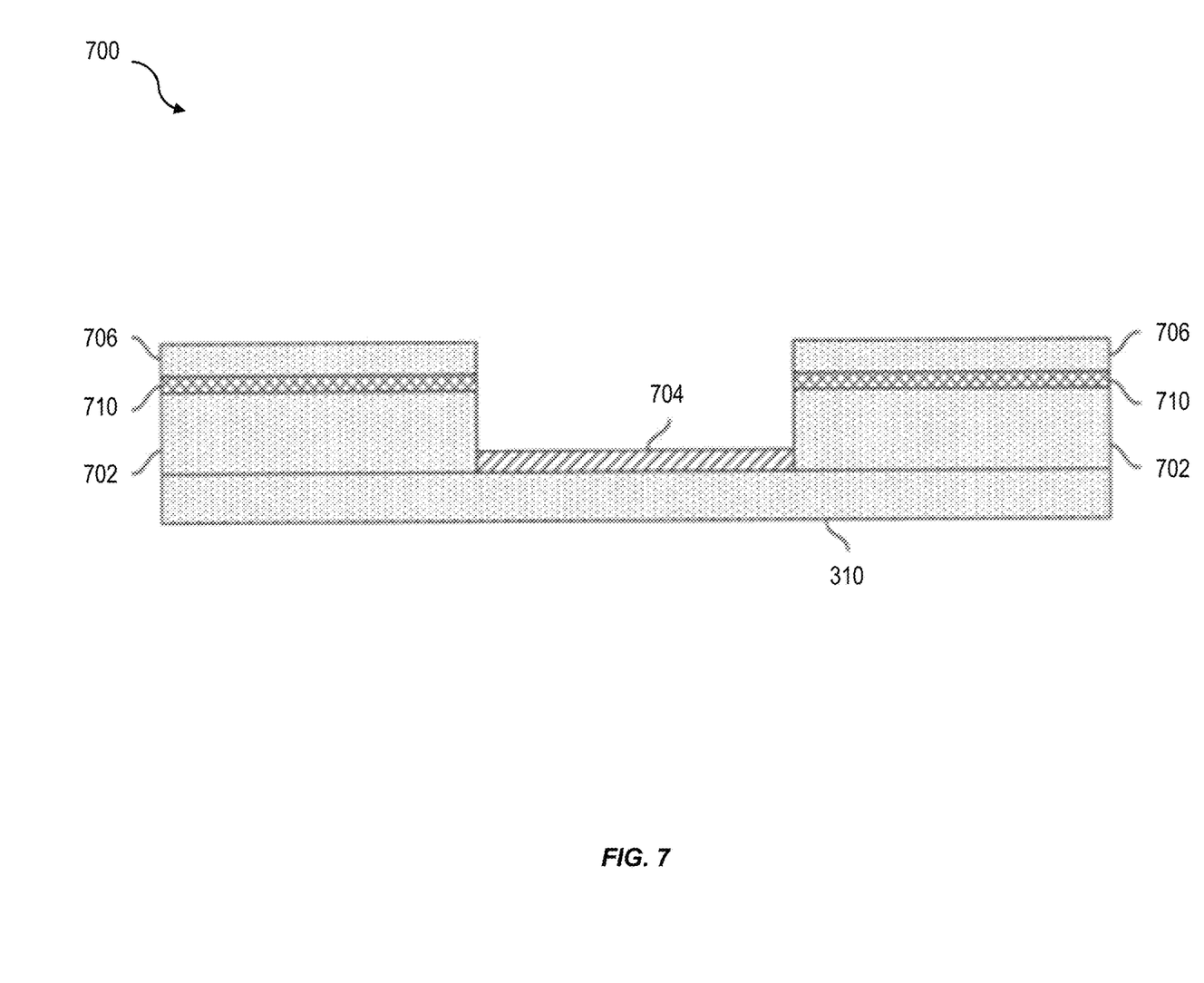
FIG. 7 shows a cross-sectional view of a portion of the RF receive coil taken along section line VIII-VIII in FIGS. 3-6.

FIG. 5 and FIG. 6 show modified ladder or "shared capacitor" implementations of a RF receive coil 210. The implementations shown in FIG. 6 and FIG. 7 are similar to the implementations shown in FIG. 3 and FIG. 4, where the RF receive coil 210 includes receive coil elements that each include a respective loop formed by a conductive line 302. However, in the implementations shown in FIG. 5 and FIG. 6, a capacitor 502 is shared by neighboring loops that form respective neighboring receive coil elements. Unlike some previously available approaches, some implementations of the current subject matter can feature two or more of the loops E1-E8 being connected at one end, for example by sharing a common conductor 504. Loops sharing a common conductor 504 can remain electrically isolated in such a configuration through the use of the shared capacitors 502. The shared capacitors 502 can be positioned outside of the treatment beam region RB by utilizing a self-cancelling arrangement of the conductive lines 302. FIG. 5 shows a 1×n shared capacitor implementation for isolating multiple receive coil elements E1, E2, and E3 from each other.

FIG. 6 shows an alternative implementation that includes a first 1×n array S1, which includes receive coil elements E1-E3, and a second 1×n array S2, which includes receive coil elements E4-E6. The first 1×n array S1 of receive coil elements E1-E3 can be formed on one side of the substrate 310, and the second 1×n array S2 of receive coil elements E4-E6 is formed on an opposite side of the substrate 310. As with the implementations shown in FIG. 3 and FIG. 4, the implementations shown in FIG. 5 and FIG. 6 can include a treatment beam area RB where there are no components, vias, or overlapping conductors on either side of the substrate 310. Also, the region WC illustrates a worst-case region where radiation can stray beyond the expected treatment beam area RB without harming the coil 210 or being subjected to components that may cause non-uniformities in the treatment beam 204. Adding the appropriate thickness of substrate 310 on each side of the substrate to compensate for the conductive lines 302 can yield a uniform attenuation to the treatment beam 204 throughout the necessary volume. The shared capacitor can also be mounted to the substrate 310 for improved packaging.

For each of the implementations disclosed herein, the treatment beam attenuation can be homogenized by placing dielectric layers in regions where the conductive lines 302 are not present in order to equalize the attenuation across the treatment beam area RB. FIG. 7 shows an exemplary cross-sectional view taken along section lines VIII-VIII shown in FIG. 3 through FIG. 6. The section shown in FIG. 7 illustrates portions of a RF coil assembly 210 that can be positioned in the path of the treatment beam 204 depending on the position of the instrument 106 relative to the RF coil assembly 210. As shown in FIG. 7, the RF coil assembly 210 can include a non-conductive (insulating) substrate 310 (e.g. a PCB) on which a first additional insulating layer 702 and a conductive layer 704 are formed. The conductive layer can include the conductive lines 302 discussed above. A second additional insulating layer 706 can be formed over the first additional insulating layer 702. The second additional insulating layer 706 can be attached to the first additional insulating layer 702 using an adhesive layer 710. Thus, since the conductive material of the conductive layer 704 and the substrate 310 together cause greater attenuation per unit thickness to the treatment beam 204 than the insulating materials of the first and second additional insulating layers 702 and 706 combined with the substrate 310 and the adhesive layer 710, the total thickness of the substrate 310, the first and second additional insulating layers 702 and 706, and the adhesive layer 710 can be greater than the total thickness of the substrate 310 and the conducting layer 704 to provide for uniform attenuation to the treatment beam 204. Other materials not shown in FIG. 7 that can be included in an RF coil assembly 210, such as additional adhesive layers, can be taken into consideration when determining appropriate thicknesses of the first and second additional insulating layers 702, 706, and/or the adhesive layer 710 for providing substantially the same attenuation as the conducting layer 704.

While each of the conducting layer 704, the substrate 310, the first and second additional insulating layers 702 and 706, and the adhesive layer 710 are shown in FIG. 7 as a single homogeneous layer, it will be understood that one or more of these structures can optionally be formed of one or more actual layers of material. Also, one or more of these structures can include one or more different materials.

In an exemplary implementation, the substrate 310 and the first and second additional insulating layers 702, 706 can be formed of KAPTON polyimide film, and the conductive layer 704 can be formed of copper. In this implementation, the total thickness of the first and second additional insulating layers 702, 706 can be chosen so as to homogenize the beam attenuation according to the attenuation caused by the copper. The relative attenuation of a material for ionizing radiation can be approximated as the product of the density of the material and the thickness of the material in a direction parallel to the propagation of the ionizing radiation. For example, assuming densities of 1.4 g·cm$^{-3}$, 8.9 g·cm$^{-3}$, and 1.2 g·cm$^{-3}$, for KAPTON (polyimide), copper, and the adhesive (disposed between the layers), respectively, and a conducting layer thickness of 0.003302 mm of the first and second insulation layers, a relative attenuation of the copper layer would be approximately equal to 0.003302 cm×8.9 g·cm$^{-3}$=0.0294 g·cm$^{-2}$. As this value is a relative attenuation, the units are not important as long as the same units for the various values are used for all layers that contribute to attenuation of the ionizing radiation. To make the relative attenuation of the parts of the receive coil assembly that do not include the conductive layer 704 at least approximately equivalent to the relative attenuation of the conductive layer 704, the sum of the thicknesses of the various layers (e.g. the first and second additional insulating layers 702, 706 and the adhesive layer 710) multiplied by the density of the material of each respective layer should be approximately equivalent to the value calculated for the conductive layer 704. In this example, if the first additional insulation layer 702, the second additional insulation layer 706, and the adhesive layer 710 have respective thicknesses of 0.0127 cm, 0.00508 cm, and 0.00254 cm, the relative attenuation of these materials is approximately equal to (0.0.0127 cm+0.00508 cm)×1.4 g·cm$^{-3}$+0.00254×1.4 g·cm$^{-3}$=0.0279 g·cm$^{-2}$. The substrate 310 and any adhesive securing the substrate 310 to the first additional insulation layer 702 can be omitted from the calculation assuming that these materials have a same thickness underlying both of the conductive layer 704 and the stack of the additional insulating layer(s).

In general, an actual layer stack-up attenuation of ionizing radiation traversing a stack of materials may be more accurately represented by a series of decaying exponentials. However, for the thicknesses used in a receive coil assembly consistent with the descriptions herein, a suitable approximation may be made of the relative attenuations using simple arithmetic. Advantageously, the relative attenuation of the insulating layers and conductive layers would be identical for perfect uniformity at least in the treatment beam region RB. However, deviations of up to a threshold amount (e.g. as much as about 5%, or perhaps as much as 10% or 15% in some cases) can provide advantages as well. While the illustrative implementation is described as including copper and KAPTON, any mix of materials and thicknesses can be used in appropriate combinations and thicknesses to result in a beam attenuation uniformity within the desired tolerance.

The RF coil assembly concepts of the present disclosure can be used with any type of magnetic resonance imaging (MRI) system. Approaches described herein can be well suited for use with a split solenoid or horizontal "open" MRI that includes a gap between two horizontal MRI magnet halves. The RF coil assemblies disclosed herein are further well suited for use with a horizontal open MRI that is used with an additional instrument being operated within its gap.

Figure 8:
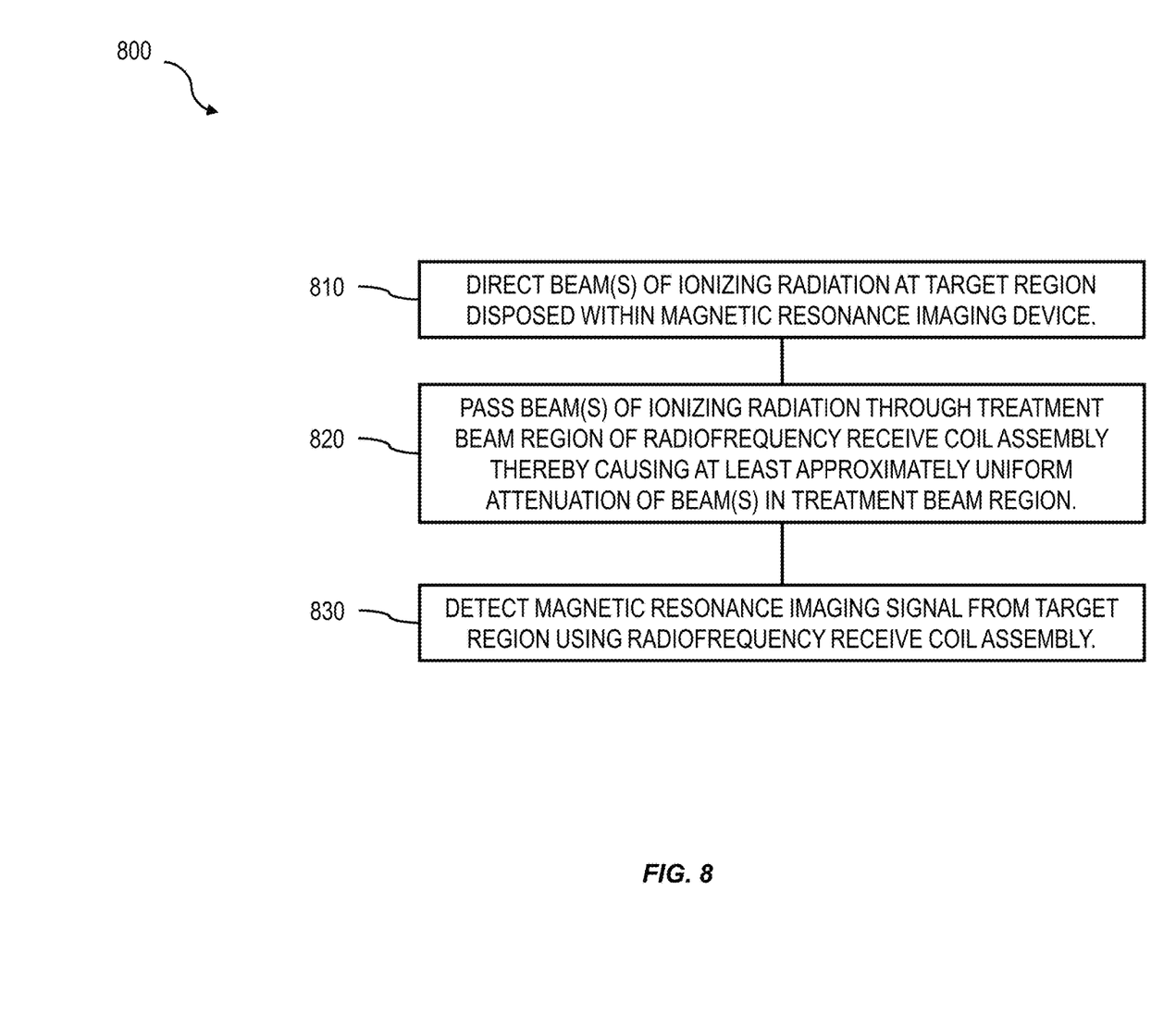
FIG. 8 shows a process flow diagram illustrating aspects of a method having one or more features consistent with implementations of the current subject matter.

FIG. 8 shows a process flow chart 800 illustrating features of a method consistent with implementations of the current subject matter. At 810, one or more beams of ionizing radiation are directed at a target region of a subject. The target region is disposed within a magnetic resonance imaging device. The one or more beams of ionizing radiation pass through a treatment beam region of a radiofrequency receive coil assembly at 820. The radiofrequency receive coil assembly causes an at least approximately uniform attenuation of the one or more beams of ionizing radiation in the treatment beam region. At 830, a magnetic resonance imaging signal is detected from the target region using the radiofrequency receive coil assembly.

The descriptions and figures provided herein disclose implementations by way of example and not by way of limitation. All numbers disclosed herein are approximate values unless stated otherwise, regardless whether the word "about" or "approximately" is used in association therewith. Whenever a numerical range with a lower limit and an upper limit is disclosed, any number falling within the range is specifically and expressly disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on,"

above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A system comprising: an instrument configured to emit a treatment beam; and a radiofrequency receive coil assembly for use in a magnetic resonance imaging system, the radiofrequency receive coil assembly comprising: a first conductive loop that extends into a treatment beam region of the radiofrequency receive coil assembly through which the treatment beam passes; and a second conductive loop that extends into the treatment beam region, the second conductive loop being electrically connected to the first conductive loop at a node, wherein the node is in the treatment beam region, and the second conductive loop overlapping the first conductive loop outside of the treatment beam region.

2. The radiofrequency receive coil assembly of claim 1, wherein the first conductive loop and the second conductive loop do not overlap each other in the treatment beam region such that the treatment beam passes through only a layer of conductive material in traversing the treatment beam region.

3. The radiofrequency receive coil assembly of claim 1, further comprising a capacitor shared by the first conducting loop and the second conducting loop.

4. The radiofrequency receive coil assembly of claim 3, wherein the first conducting loop and the second conducting loop share a common conductor and wherein the capacitor provides electrical isolation between the first conducting loop and the second conducting loop.

5. The radiofrequency receive coil assembly of claim 1, wherein the treatment beam region is free of any capacitors.

6. The radiofrequency receive coil assembly of claim 1, further comprising a substrate that supports the first conductive loop, the second conductive loop, and an insulating region.

7. The radiofrequency receive coil assembly of claim 6, wherein at least one of the insulating layer and the substrate comprises polyimide.

8. The radiofrequency receive coil assembly of claim 6, further comprising a third conductive loop, wherein the first and second conductive loops are disposed on a first side of the substrate, and the third conductive loop is disposed on a second side of the substrate.

9. The radiofrequency receive coil assembly of claim 8, wherein the third conductive loop extends into the treatment beam region.

10. The radiofrequency receive coil assembly of claim 1, wherein the first conductive loop and/or second conductive loop comprises at least one of copper, silver, and aluminum.

11. The radiofrequency receive coil assembly of claim 1, wherein a linear distance separates centers of the first conducting loop and the second conducting loop, the linear distance being sufficient to cause a mutual inductance between the first conducting loop and the second conducting loop to be below 5% of the inductance of the first conducting loop and the second conducting loop.

12. The radiofrequency receive coil assembly of claim 11, wherein the linear distance is sufficient to cause the mutual inductance between the first conducting loop and the second conducting loop to be below 1% of the inductance of the first conducting loop and the second conducting loop.

13. The radiofrequency receive coil assembly of claim 1, further comprising an insulating region disposed within the treatment beam region, the insulating region comprising at least one layer of an insulating material having a thickness sufficient to cause attenuation of the treatment beam in the insulating region to be at least approximately equal to attenuation of the treatment beam by the layer of conductive material.

14. A magnetic resonance imaging-radiotherapy system comprising: an instrument configured to emit a treatment beam; and a magnetic resonance imaging system, the magnetic resonance imaging system comprising a radiofrequency receive coil assembly, which comprises: a first conductive loop that extends into a treatment beam region of the radiofrequency receive coil assembly through which the treatment beam passes; and a second conductive loop that extends into the treatment beam region, the second conductive loop being electrically connected to the first conductive loop at a node, wherein the node is in the treatment beam region, and the second conductive loop overlapping the first conductive loop outside of the treatment beam region.

15. The magnetic resonance imaging-radiotherapy system of claim 14, wherein the magnetic resonance imaging-radiotherapy system comprises a split magnetic resonance imaging system, which comprises first and second magnet housings separated by a gap region, a gantry disposed in the gap region, at least one radiotherapy head disposed on and moveable with the gantry, and a patient couch configured to support a subject within the first and second magnet housings; and
    wherein the split magnetic resonance imaging system comprises the radiofrequency receive coil assembly.

16. The magnetic resonance imaging-radiotherapy system of claim 14, further comprising a capacitor shared by the first conducting loop and the second conducting loop, wherein the first conducting loop and the second conducting loop share a common conductor and wherein the capacitor provides electrical isolation between the first conducting loop and the second conducting loop.

17. The magnetic resonance imaging-radiotherapy system of claim 14, wherein the first conductive loop and the second conductive loop do not overlap each other in the treatment beam region such that the treatment beam passes through only a layer of conductive material in traversing the treatment beam region.

18. The magnetic resonance imaging-radiotherapy system of claim 14, further comprising an insulating region disposed within the treatment beam region, the insulating region comprising at least one layer of an insulating material having a thickness sufficient to cause attenuation of the treatment beam in the insulating region to be at least approximately equal to attenuation of the treatment beam by the layer of conductive material.

* * * * *